United States Patent

Begley et al.

[11] Patent Number: 5,962,656
[45] Date of Patent: Oct. 5, 1999

[54] INDAZOLE CONTAINING COUPLER

[75] Inventors: William James Begley, Webster; Teh Hsuan Chen, Fairport; Donald Singleton, Jr., Rochester; Frank Dino Coms, Fairport, all of N.Y.

[73] Assignee: Eastman Kodak Company, Rochester, N.Y.

[21] Appl. No.: 08/872,118

[22] Filed: Jun. 10, 1997

Related U.S. Application Data

[62] Division of application No. 08/590,661, Jan. 24, 1996, Pat. No. 5,686,234.
[60] Provisional application No. 60/000,766, Jun. 30, 1995, and provisional application No. 60/002,984, Aug. 30, 1995.

[51] Int. Cl.[6] .................... C07D 403/12; C07D 403/14; C07D 231/56
[52] U.S. Cl. .................... 534/651; 544/140; 546/269.4; 548/136; 548/144; 548/217; 548/251; 548/259; 548/261; 548/362.5
[58] Field of Search ................ 548/251, 362.5, 548/136, 144, 217, 259, 261; 534/651; 544/140; 546/269.4

[56] References Cited

U.S. PATENT DOCUMENTS

| | | | |
|---|---|---|---|
| 4,248,962 | 2/1981 | Lau | 430/382 |
| 4,409,323 | 10/1983 | Sato et al. | 430/544 |
| 4,639,408 | 1/1987 | Kitaguchi et al. | 430/351 |
| 4,783,396 | 11/1988 | Nakamura et al. | 430/353 |
| 4,861,701 | 8/1989 | Burns et al. | 430/543 |
| 5,026,628 | 6/1991 | Begley et al. | 430/382 |

FOREIGN PATENT DOCUMENTS

| | | |
|---|---|---|
| 393720 | 10/1990 | European Pat. Off. |
| 0 464 612 | 1/1992 | European Pat. Off. |
| 0 499 279 | 2/1992 | European Pat. Off. |
| 0 514 896 | 11/1992 | European Pat. Off. |
| 0 529 436 | 3/1993 | European Pat. Off. |
| 0 576 088 | 12/1993 | European Pat. Off. |
| 0 438 129 | 4/1995 | European Pat. Off. |
| 57-056837 | 4/1982 | Japan. |

*Primary Examiner*—Laura L. Stockton
*Attorney, Agent, or Firm*—Sarah Meeks Roberts

[57] ABSTRACT

A photographic element comprising a support having situated thereon at least one silver halide emulsion layer, the layer containing a photographic coupler represented by the formula

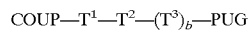

wherein
COUP is a coupler moiety having a coupling site to which $T^1$ is attached;
$T^1$ and T3 are timing or linking groups;
$T^2$ is an indazole timing or linking group which, after release from $T^1$, functions by electron transfer down a conjugated chain to release $T^3$ or PUG, and which is represented by the formula:

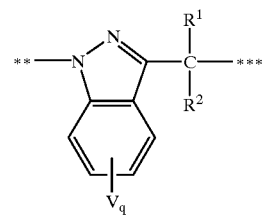

wherein  denotes the point of attachment to $T^1$ and * denotes the point of attachment to $T^3$ or PUG;
$R^1$ and $R^2$ are independently selected from hydrogen, or an aliphatic, carbocyclic, or heterocyclic group, or may be bonded together to form a 5, 6, or 7 membered ring;
V is independently a substituent group as further defined;
q is 0, 1, 2, 3 or 4;
b is 0 or 1; and
PUG is a photographically useful group.

2 Claims, No Drawings

INDAZOLE CONTAINING COUPLER

CROSS REFERENCE TO RELATED APPLICATION

This is a Divisional of application Ser. No. 08/590,661, filed Jan. 24, 1996, now U.S. Pat. No. 5,686,234, for which reference is made to and priority claimed from U.S. Provisional Application Ser. No. 60/000,766, filed Jun. 30, 1995, entitled PHOTOGRAPHIC ELEMENT CONTAINING A COUPLER CAPABLE OF RELEASING A PHOTOGRAPHICALLY USEFUL GROUP and U.S. Provisional Application Ser. No. 60/002,984, filed Aug. 30, 1995, entitled PHOTOGRAPHIC ELEMENT CONTAINING A COUPLER CAPABLE OF RELEASING A PHOTOGRAPHICALLY USEFUL GROUP.

FIELD OF THE INVENTION

This invention relates to photographic elements, processes and couplers, the couplers being of the type that release a photographically useful group (PUG) through a series of timing or linking groups upon reaction with oxidized color developing agent during processing.

BACKGROUND OF THE INVENTION

Various ways are recognized in the photographic industry for releasing a PUG from a compound, such as a coupler, in a photographic material and process. Release can be direct, for example upon reaction of the coupler with oxidized color developing agent during processing, or it can be indirect through a linking or timing group. Linking and timing groups provide the ability to control the timing and rate of release of a PUG in a photographic element, as well as the rate and distance of diffusion of the PUG in the element during processing.

U.S. Pat. No. 4,248,962 describes compounds that release a PUG, such as a development inhibitor group, through a timing group which functions by (intramolecular) nucleophilic displacement reaction. Other examples of compounds that are capable of releasing a PUG are described in European Patent Application 0 514 896 and in U.S. Pat. Nos. 4,409,323 and 4,861,701. In European Patent Application 0 514 896, compounds are described which release a PUG through a timing or linking group which functions by electron transfer down an unconjugated chain. In U.S. Pat. No. 4,409,323, compounds are described which release a PUG by a mechanism which involves electron transfer down a conjugated chain. In U.S. Pat. No. 4,861,701, sequences of timing groups are utilized to release a PUG and to provide desirable control over the impact of the PUG on photographic properties.

European Patent Applications 0 499 279 and 0 438 129 describe photographic couplers which allegedly provide superior release rates over compounds described in the aforementioned U.S. Pat. No. 4,861,701. Specifically, these applications describe photographic couplers having a heterocyclic timing nucleus (typically pyrazole) attached to a coupler moiety through an —O—C(O)— or —OCH$_2$— group, or other group capable of releasing the heterocyclic timing nucleus by electron transfer down an unconjugated chain. A development inhibitor moiety is attached to the 4-position of the heterocyclic timing nucleus and is released therefrom upon reaction of the couplers with oxidized color developing agent during processing.

The compounds described in the above European Patent Applications do not provide for any flexibility in their rate of release of a PUG, or in their synthetic design, as they are limited by the presence of the particular first timing or linking group. More importantly, though, it was determined that the compounds in both of these applications exhibit poor stability and decompose when stored for prolonged periods under tropical conditions. Thus, they are of limited practical value in today's photographic industry.

The present inventors therefore sought to improve upon the couplers described in the aforementioned European Patent Applications and to provide alternative means by which to release photographically useful groups in a controlled manner to photographic emulsions. In so doing, the inventors synthesized couplers having pyrazole timing groups wherein the PUG was attached through other than the 4-position. It was determined, however, that although such couplers were generally stable when stored upon tropical conditions for prolonged periods of time, and were synthetically simple to manufacture, they exhibited a relatively low photographic activity—that is, they failed to release their PUG at an efficient rate. An effort was therefore undertaken to determine how the activity of these couplers could be improved.

SUMMARY OF THE INVENTION

The present inventors discovered that substantial improvements in the activity of couplers containing a 3-substituted pyrazole timing group can be achieved when such a timing group is fused with a phenyl substituent to form an indazole timing group. In accordance with this discovery, the inventors have provided a photographic coupler as described below, and a photographic element comprising a support having situated thereon at least one silver halide emulsion layer, the layer containing a photographic coupler represented by the formula:

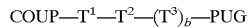

wherein
COUP is a coupler moiety having a coupling site to which T$^1$ is attached;

T$^1$ is a timing or linking group which releases from COUP during processing and which functions by electron transfer down a conjugated or unconjugated chain, or by nucleophilic displacement reaction, to release T$^2$, T$^2$ being an indazole timing or linking group which, after release from T$^1$, functions by electron transfer down a conjugated chain to release T$^3$ or PUG, and which is represented by the formula:

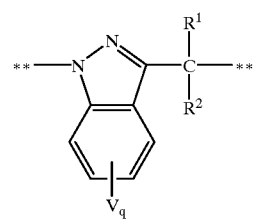

wherein  denotes the point of attachment to T$^1$ and * denotes the point of attachment to T$^3$ or PUG;

R$^1$ and R$^2$ are independently selected from hydrogen, or an aliphatic, carbocyclic, or heterocyclic group, or may be bonded together to form a 5, 6, or 7 membered ring;

V is independently selected from the group consisting of an alkyl, carbocyclic, heterocyclic, halo, carbamoyl, sulfamoyl, carbonamido, sulfonamido, keto, sulfo, nitro, hydroxyl, carboxyl, amino, alkoxy, alkoxycarbonyl, aryloxy, or arylthio group;

q is 0, 1, 2, 3 or 4;

$T^3$ is a timing or linking group attached to $T^2$ which is released therefrom after $T^2$ releases from $T^1$, and which functions by electron transfer down a conjugated or unconjugated chain, or by nucleophilic displacement reaction, to release PUG;

b is 0 or 1; and

PUG is a photographically useful group.

Also provided is a process of forming an image in an exposed photographic silver halide element containing a coupler as described above comprising developing the element with a color photographic silver halide developing agent.

The invention provides the opportunity to achieve improved image modification through the use of a new type of coupler capable of releasing a PUG upon photographic processing. The new coupler is stable when stored for prolonged periods of tropical conditions, is synthetically simple to manufacture, and provides for the release of a PUG at a desired rate. The coupler utilized in the invention, particularly when PUG is a development inhibitor, can provide increased acutance and improved contrast effects in photographic elements in which it is contained.

DETAILED DESCRIPTION OF THE INVENTION

In the photographic coupler utilized in accordance with the present invention, the coupler moiety, as represented by COUP, can be any moiety that will react with oxidized color developing agent during processing to cleave the bond between $T^1$ and the coupler moiety. The coupler moiety as described herein includes conventional coupler moieties employed to yield both colorless and colored products upon reaction with oxidized color developing agents. Both types of coupler moieties are well known to those skilled in the photographic art and are exemplified in, for example, *Research Disclosure*, September 1994, Item 36544, all published by Kenneth Mason Publications, Ltd., Dudley Annex, 12a North Street, Emsworth, Hampshire PO10 7DQ, ENGLAND.

Representative coupler moieties suitable for use in the invention are as follows:

COUP

A. Coupler moieties which form cyan dye upon reaction with oxidized color developing agent are described in such representative patents and publications as: U.S. Pat. Nos. 2,772,162; 2,895,826; 3,002,836; 3,034,892; 2,474,293; 2,423,730; 2,367,531; 3,041,236; 4,333,999 and "Farbkuppler-eine Literaturubersicht," published in Agfa Mitteilungen, Band III, pp. 156–175 (1961), all of which are incorporated herein by reference.

Preferably such cyan dye-forming coupler moieties are phenols and naphthols.

B. Coupler moieties which form magenta dye upon reaction with oxidized color developing agent are described in such representative patents and publications as: U.S. Pat. Nos. 2,600,788; 2,369,489; 2,343,703; 2,311,082; 3,152,896; 3,519,429; 3,062,653; 2,908,573 and "Farbkuppler-eine Literaturubersicht," published in Agfa Mitteilungen, Band III, pp. 126–156 (1961), all of which are incorporated herein by reference.

Preferably such magenta dye-forming coupler moieties are pyrazolones or pyrazolotriazoles.

C. Coupler moieties which form yellow dye upon reaction with oxidized color developing agent are described in such representative patents and publications as: U.S. Pat. Nos. 2,875,057; 2,407,210; 3,265,506; 2,298,443; 3,048,194; 3,447,928 and "Farbkuppler-eine Literaturubersicht," published in Agfa Mitteilungen, Band III, pp. 112–126 (1961), all of which are incorporated herein by reference.

Preferably such yellow dye-forming coupler moieties are acylacetamides, such as benzoylacetamides and pivaloylacetamides.

D. Coupler moieties which form a colorless product upon reaction with oxidized color developing agent are described in such representative patents as: U.K. Patent No. 861,138; and U.S. Pat. Nos. 3,632,345; 3,928,041; 3,958,993 and 3,961,959, all of which are incorporated herein by reference.

Specific representative examples of coupler moieties suitable for use in the invention are as follows:

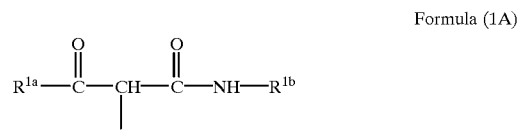

Formula (1A)

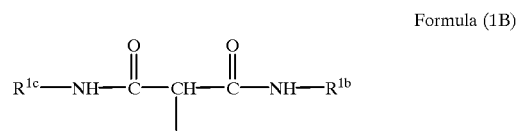

Formula (1B)

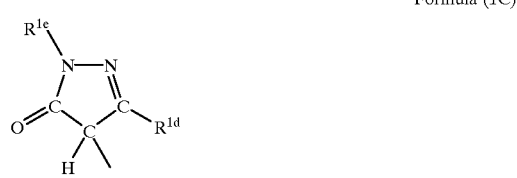

Formula (1C)

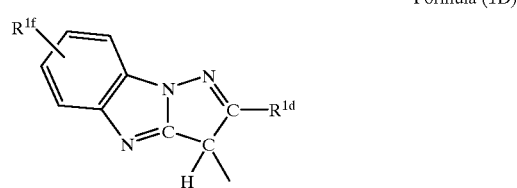

Formula (1D)

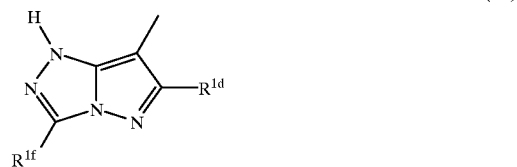

Formula (1E)

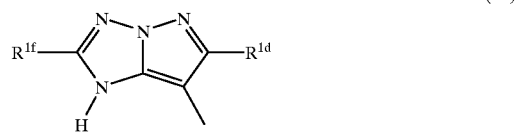

Formula (1F)

-continued

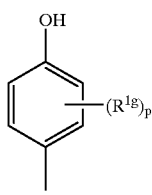

Formula (1G)

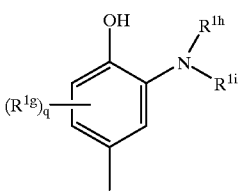

Formula (1H)

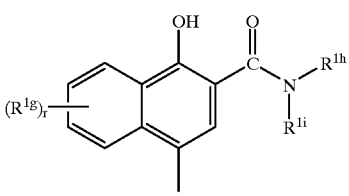

Formula (1I)

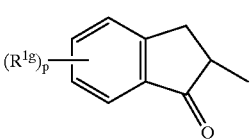

Formula (1J)

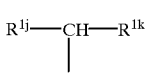

Formula (1K)

The free bond in each of the coupler moieties described above represents the coupling site, which is the position to which $T^1$ and the coupling-off group is linked.

In the above formulae, $R^{1a}$, $R^{1b}$, $R^{1c}$, $R^{1d}$, $R^{1e}$, $R^{1f}$, $R^{1g}$, $R^{1h}$, $R^{1i}$, $R^{1j}$, or $R^{1k}$ may help form, or may contain one or more solubilizing groups which will enable the coupler, upon reaction with oxidized color developing agent, to form a dye or colorless compound capable of being washed out of the photographic element during processing. Such groups, and couplers containing them, are exemplified in U.S. Pat. Nos. 4,482,629; 5,026,628; 5,151,343; 5,250,398; and 5,250,399, which are incorporated herein by reference. Specifically preferred solubilizing groups are selected from a carboxyl, sulfo, carbonamido or hydroxyl group, or salt thereof. It is preferred that when a solubilizing group is present, the coupler is also unballasted so that complete washing out of the coupler can occur. By unballasted, it is meant that each $R^{1a}$ to $R^{1k}$ contain no more than 20 carbon atoms, preferably no more than 12 carbon atoms, and optimally no more than 8 carbon atoms.

$R^{1a}$ to $R^{1k}$, p, q and r in formulae (1A) to (1K) are set forth in more detail as follows. Each of $R^{1a}$ to $R^{1k}$ can be independently selected from the group consisting of hydrogen, or a substituted or unsubstituted aliphatic, carbocyclic or heterocyclic group. Aliphatic, carbocyclic, and heterocyclic groups as used herein and elsewhere in this application are defined in accordance with the definitions set forth in Grant and Hackh's *Chemical Dictionary*, fifth ed., McGraw-Hill 1987, and are in accordance with general rules of chemical nomenclature.

Exemplary aliphatic groups include alkyl, alkene, and alkyne groups, specifically methyl, ethyl, propyl, butyl, pentyl, hexyl, octyl, nonyl, decyl, dodecyl, hexadecyl, octadecyl, isopropyl, t-butyl, butenyl, pentenyl, hexenyl, octenyl, dodecenyl, propynyl, butynyl, pentynyl, hexynyl, and octynyl.

Exemplary carbocyclic groups (which include aryl groups) are phenyl, tolyl, naphthyl, cyclohexyl, cyclopentyl, cyclohexenyl, cycloheptatrienyl, cyclooctatrienyl, cyclononatrienyl, cyclopentenyl, anilinyl, and anisidinyl.

Exemplary heterocyclic groups (which include heteroaryl groups) are pyrrolyl, furanyl, tetrahydrofuranyl, pyridinyl, picolinyl, piperidinyl, morpholinyl, thiadiazolyl, thiatriazolyl, benzothiazolyl, benzoxazolyl, benzimidizolyl, benzoselenozolyl, benzotriazolyl, indazolyl, quinolinyl, quinaldinyl, pyrrolidinyl, thiophenyl, oxazolyl, thiazolyl, imidazolyl, selenazolyl, tellurazolyl, triazolyl, tetrazolyl, and oxadiazolyl.

Groups suitable for substitution on each of the above include alkyl and alkylene groups (for example, methyl, ethyl, ethylene, hexyl, hexylene), fluoroalkyl groups (for example, trifluoromethyl), alkoxy groups (for example, methoxy, ethoxy, octyloxy), aryl groups (for example, phenyl, naphthyl, tolyl), hydroxy groups, halogen groups, aryloxy groups (for example, phenoxy), alkylthio groups (for example, methylthio, butylthio), arylthio groups (for example, phenylthio), acyl groups (for example, acetyl, propionyl, butyryl, valeryl), sulfonyl groups (for example, methylsulfonyl, phenylsulfonyl), acylamino groups, sulfonylamino groups, acyloxy groups (for example, acetoxy, benzoxy), carboxy groups, cyano groups, sulfo groups, and amino groups.

p in the above formulae can be an integer of 1 to 4; q can be an integer of 1 to 3; and r can be an integer of 1 to 5.

Preferred coupler moieties suitable for the couplers utilized in the invention are represented by:

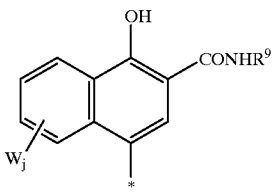

wherein

* denotes the coupling site to which $T^1$ is attached;

$R^9$ is selected from hydrogen, or an aliphatic, carbocyclic, or heterocyclic group; and is preferably selected from hydrogen, an alkyl group containing 1–5 carbon atoms, an aryl group containing 6–10 carbon atoms or a heterocyclic group containing 4–8 carbon atoms;

W is selected from an alkyl, heterocyclic, halo, carbamoyl, sulfamoyl, carbonamido, sulfonamido, keto, sulfo, nitro, hydroxyl, carboxyl, amino, alkoxy, alkoxycarbonyl, aryloxy, or arylthio, group; and is preferably selected from an alkyl containing 1–5 carbon atoms or a carbamoyl, sulfamoyl, carbonamido, sulfonamido, sulfo, nitro, hydroxyl, carboxyl, amino, alkoxy or alkoxycarbonyl group; and j is 0, 1, 2, 3, or 4, preferably 0 or 1.

Also preferred are coupler moieties represented by:

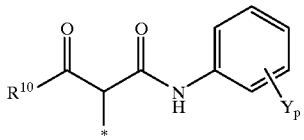

wherein

* denotes the coupling site to which $T^1$ is attached;

$R^{10}$ is selected from an aliphatic, carbocyclic, or heterocyclic group; and is preferably selected from an alkyl group containing 1–10 carbon atoms, an aryl group containing 6–10 carbon atoms or a heterocyclic group containing 4–8 carbon atoms;

Y is selected from an alkyl, heterocyclic, halo, carbamoyl, sulfamoyl, carbonamido, sulfonamido, keto, sulfo, nitro, hydroxyl, carboxyl, amino, alkoxy, alkoxycarbonyl, aryloxy or arylthio group; and is preferably selected from an alkyl containing 1–5 carbon atoms, carbamoyl, sulfamoyl, carbonamido, sulfonamido, sulfo, nitro, hydroxyl, carboxyl, amino, alkoxy or alkoxycarbonyl group; and p is 0, 1, 2, 3, or 4, preferably 1 or 2.

The photographic coupler utilized in the invention reacts (i.e. couples) with the oxidized product of a color developing agent during processing to release $T^1$-$T^2$-$(T^3)_b$-PUG. $T^1$ and $T^3$ can be any of the timing or linking groups known in the art, for instance those described below and in U.S. Pat. Nos. 4,248,962; 4,409,323; 4,421,845; 4,861,701; 4,864,604; 5,034,311; 5,055,385; and European Patent Application 0 167 168, all of which are incorporated herein by reference. Thus, they independently may be timing or linking groups which function by nucleophilic displacement reaction (of the type described in, for example, U.S. Pat. No. 4,248,962) or electron transfer down a conjugated chain (of the type described in, for example, U.S. Pat. No. 4,861,701). They may also be timing or linking groups which function by electron transfer down an unconjugated chain. These last groups are known in the art under various names. Often they have been referred to as groups capable of utilizing a hemiacetal or iminoketal cleavage reaction or groups capable of utilizing a cleavage reaction due to ester hydrolysis. Regardless of their label, though, their mechanism is that of electron transfer down an unconjugated chain which results, typically, in a relatively fast decomposition and the production of carbon dioxide, formaldehyde or other low molecular weight byproducts. The groups are exemplified specifically in European Patent Applications 0 464 612 and 0 523 451, both of which are incorporated herein by reference.

$T^1$ and $T^3$ function as described above to release $T^2$ and the PUG, respectively. The timing or linking group $T^2$, once released from $T^1$ undergoes electron transfer through the indazole moiety resulting in cleavage of the bond between $T^2$ and $T^3$, when b is 1, or between $T^2$ and PUG, when b is 0.

Representative $T^1$ and $T^3$ groups can be selected from the following:

Timing or Linking Groups, ($T^1$ and $T^3$)

1. Acyclic timing or linking groups capable of nucleophilic displacement reaction:

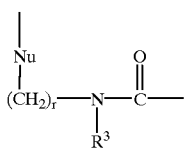

where r is 0 to 5; preferably 2, 3 or 4; Nu is a nucleophilic group, typically

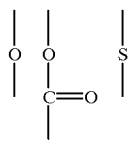

and $R^3$ is hydrogen, or an aliphatic, carbocyclic, or heterocyclic group. Preferably, it is hydrogen, an alkyl of 1 to 20 carbon atoms or aryl of 6 to 20 carbon atoms. More preferably, it is hydrogen, an alkyl of 1 to 4 carbon atoms or an aryl of 6 to 10 carbon atoms.

2. Aromatic timing and linking groups capable of nucleophilic displacement reaction:

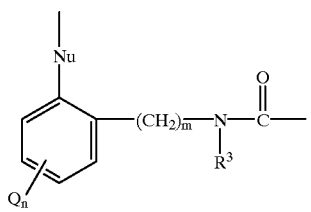

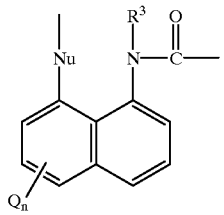

where m is 0, 1, 2 or 3, preferably 0 or 1; and Nu is a nucleophilic group, typically selected from

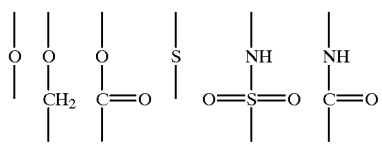

$R^3$ is as defined above; Q is independently selected from the group consisting of an alkyl, heterocyclic, halo, carbamoyl, sulfamoyl, carbonamido, sulfonamido, keto, sulfo, nitro, hydroxyl, carboxyl, amino, alkoxy, alkoxycarbonyl, aryloxy, or arylthio group; and n is an integer selected from 0, 1, 2 or 3.

Preferably, Q is an alkyl of 1 to 4 carbon atoms, or a nitro, sulfo, carbonamido or sulfonamido group, and n is 0 or 1.

3. Heterocyclic timing and linking groups capable of nucleophilic displacement reaction:

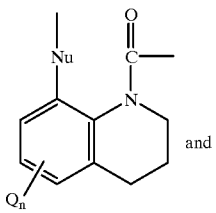

and

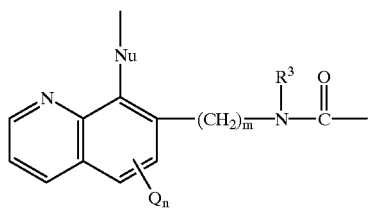

where m, n, Q, Nu and $R^3$ are as defined above.

4. Aromatic timing and linking groups capable of electron transfer down a conjugated chain:

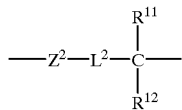

where $Z^2$ is oxygen, sulfur or an unsubstituted or lower alkyl ($C_1$–$C_5$) substituted nitrogen; $L^2$ is a pyridylene, 1,2- or 1,4-phenylene or naphthalene group; and $R^{11}$ and $R^{12}$ are independently selected from a hydrogen, or an alkyl or aryl group, preferably one containing fewer than 10 carbon atoms.

5. Timing and linking groups capable of electron transfer down an unconjugated chain:

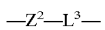

wherein $Z^2$ is oxygen, sulfur or an unsubstituted or lower alkyl ($C_1$–$C_5$) substituted nitrogen; and $L^3$ is a bivalent group selected from:

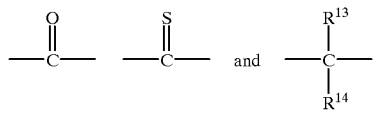

where $R^{13}$ and $R^{14}$ are independently a hydrogen, alkyl or aryl group, and are preferably hydrogen.

In one preferred embodiment of the invention, $T^1$ and $T^3$ are timing or linking groups which function by nucleophilic displacement reaction. Since in this embodiment both function by the same mechanism, in subsequent discussions of the timing and linking groups $T^1$ and $T^3$, reference will be made to nucleophilic groups $Nu^1$ and $Nu^2$, linking groups $X^1$ and $X^2$, and electrophilic groups $E^1$ and $E^2$. When describing $T^1$, $Nu^1$, $X^1$ and $E^1$ will be used; and when describing $T^3$, $Nu^2$, $X^2$ and $E^2$ will be used. $Nu^1$ may be different from $Nu^2$; $X^1$ may be different from $X^2$; and $E^1$ may be different from $E^2$. Representative examples of nucleophilic groups, electrophilic groups and linking groups can be found in U.S. Pat. No. 4,248,962, previously incorporated by reference.

$T^1$ in this embodiment thus comprises a nucleophilic group ($Nu^1$)—which is attached to the coupling site of COUP and which is displaced therefrom upon reaction of COUP with oxidized color developing agent during processing—and an electrophilic group ($E^1$)—which is attached to the indazole moiety $T^2$, and which is displaced therefrom by $Nu^1$ after $Nu^1$ is displaced from COUP.

$T^3$ comprises a nucleophilic group ($Nu^2$)—which is attached to the indazole moiety $T^2$ and which is displaced therefrom upon cleavage of the bond between $E^1$ and $T^2$ and the subsequent transfer of electrons down the conjugated chain of $T^2$—and an electrophilic group ($E^2$)—which is attached to the PUG, and which is displaced therefrom by $Nu^2$ after $Nu^2$ is displaced from $T^2$.

The nucleophilic and electrophilic groups in $T^1$ and $T^3$ are separated from each other by linking groups ($X^1$ in $T^1$ and $X^2$ in $T^3$). The linking group $X^1$ spatially relates the nucleophilic group $Nu^1$ from the electrophilic group $E^1$ so that upon displacement of the nucleophilic group from the coupler moiety, $T^1$ undergoes a nucleophilic displacement reaction with the formation of, preferably, a three to eight membered ring and the cleavage of the bond between the electrophilic group $E^1$ and $T^2$.

The linking group $X^2$ spatially relates the nucleophilic group $Nu^2$, from the electrophilic group $E^2$ so that upon displacement of the nucleophilic group from $T^2$, $T^3$ undergoes a nucleophilic displacement reaction with the formation of, preferably, a three to eight membered ring and the cleavage of the bond between the electrophilic group $E^2$ and the PUG.

The preferred couplers utilized in this embodiment of the invention can therefore be represented by the formula:

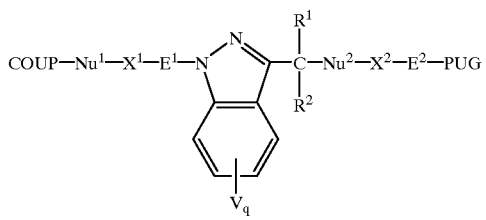

wherein COUP, $Nu^1$, $Nu^2$, $X^1$, $X^2$, $E^1$, $E^2$, V, q and PUG are as defined above. $R^1$ and $R^2$ are also defined above and are independently selected from hydrogen, or an aliphatic, carbocyclic, or heterocyclic group, or may be bonded together to form a 5, 6 or 7 membered ring. By 5, 6 or 7 membered ring it is meant any of the carbocyclic or heterocyclic rings previously described that comprise the requisite number of carbon or hetero atoms in their ring structure. Preferably, $R^1$ and $R^2$ are independently selected from hydrogen or an alkyl having from 1 to 8 carbon atoms.

More preferably, the couplers are represented by the formula:

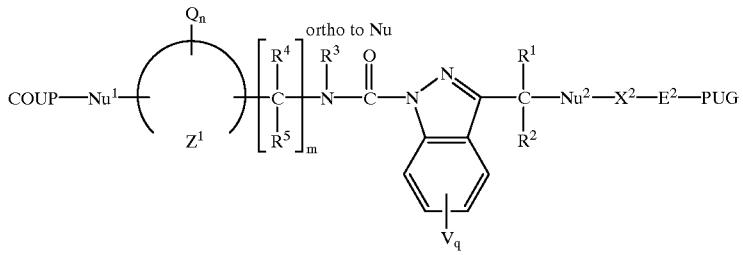

wherein COUP, $Nu^1$, $Nu^2$, $X^2$, $E^2$, $R^1$, $R^2$, V, q and PUG are as defined above. $Q_n$ in such a coupler is also as described above, with n being from 0 to 3; that is Q is selected from the group consisting of an alkyl, heterocyclic, halo, carbamoyl, sulfamoyl, carbonamido, sulfonamido, keto, sulfo, nitro, hydroxyl, carboxyl, amino, alkoxy, alkoxycarbonyl, aryloxy, or arylthio group.

$Z^1$ represents the atoms necessary to complete a mono or bicyclic aromatic or heterocyclic ring system containing 5 to 10 ring atoms, such as those described previously for heterocyclic and carbocyclic groups in the definition of coupler moieties. $R^3$, $R^4$ and $R^5$ are independently selected from hydrogen, or an aliphatic, carbocyclic, or heterocyclic group, or two of $R^3$, $R^4$ and $R^5$ may be bonded together in a pair to form a 5, 6, or 7 membered ring. And m is selected from 0, 1, 2 or 3.

Another preferred coupler is represented by the formula:

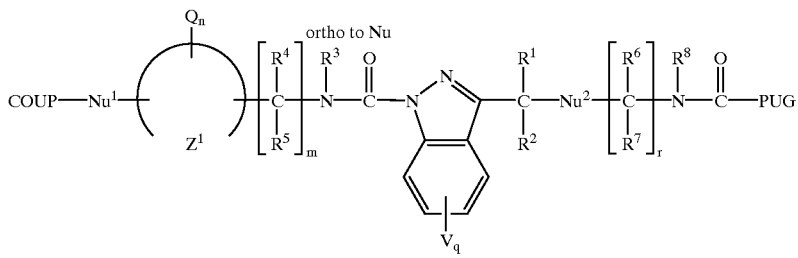

wherein COUP, $Nu^1$, $Nu^2$, $Z^1$, Q, $R^1$, $R^2$, V, q, m and PUG are as defined above; $R^3$, $R^4$ and $R^5$ are independently selected from hydrogen, or an aliphatic, carbocyclic, or heterocyclic group, or two of $R^3$, $R^4$, or $R^5$ may be bonded together in a pair to form a 5, 6, or 7 membered ring; $R^6$, $R^7$ and $R^8$ are independently selected from hydrogen, or an aliphatic, carbocyclic or heterocyclic group, or two of $R^6$, $R^7$ or $R^8$ may be bonded together to form a 5, 6 or 7 membered ring; and r is selected from 0, 1, 2, 3, 4 or 5, and is preferably 1, 2, 3 or 4.

In another preferred embodiment of the invention, $T^1$ is a timing or linking group which functions by electron transfer down an unconjugated chain and $T^3$ is absent, or is a timing or linking group which functions by nucleophilic displacement reaction.

Couplers utilized in this embodiment of the invention can be represented by the formula:

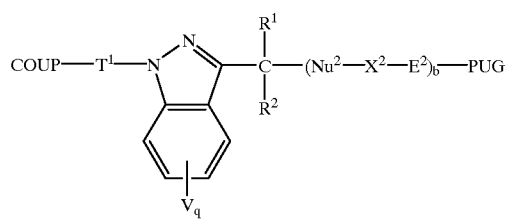

wherein COUP, $Nu^2$, $X^2$, $E^2$, $R^1$, $R^2$, V, q, b and PUG are as defined above. $T^1$ is a timing or linking group which functions by electron transfer down an unconjugated chain and is preferably of the formula:

$$-Z^2-L^3-$$

wherein $Z^2$ is oxygen, sulfur or an unsubstituted or lower alkyl ($C_1$–$C_5$) substituted nitrogen; and $L^3$ is a bivalent group selected from:

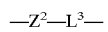

where $R^{13}$ and $R^{14}$ are independently a hydrogen, alkyl or aryl group, and are preferably hydrogen.

Preferably $T^1$ is selected from the group consisting of:

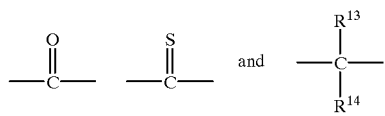

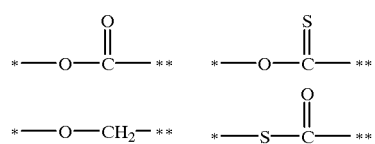

-continued

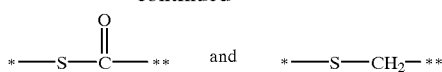

wherein * denotes the point of attachment of $T^1$ to COUP and ** denotes the point of attachment of $T^1$ to the indazole moiety, $T^2$.

More preferably, $T^1$ is a timing or linking group selected from the group consisting of:

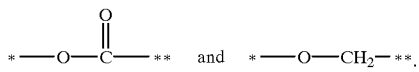

The preferred couplers utilized in this embodiment of the invention are represented by the formula:

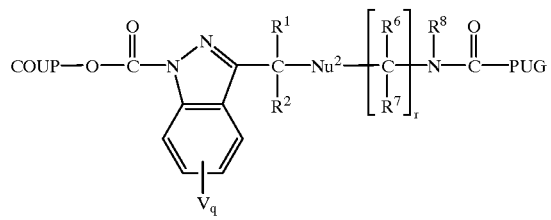

wherein COUP, V, $R^1$, $R^2$, $R^6$, $R^7$, $R^8$, $Nu^2$, r, q and PUG are as defined above.

The coupler utilized in the invention releases a PUG precursor upon coupling during processing. The PUG can be any PUG known in the art. Examples include development inhibitors, bleach accelerators, development accelerators, dyes, bleach inhibitors, couplers, developers, silver complexing agents, fixing agents, image toners, stabilizers, hardeners, tanning agents, fogging agents, ultraviolet radiation absorbers, antifoggants, nucleators, chemical or spectral sensitizers, and desensitizers. Other PUGs known in the art are also possible in the present invention.

In the preferred embodiment of the invention the PUG is a development inhibitor. Couplers which release development inhibitors can enhance the effects heretofore obtained with untimed or unlinked DIR couplers since they can release a development inhibitor at a distance from the point at which oxidized color developing agent reacted with the coupler, in which case they can provide, for example, enhanced interlayer interimage effects.

Specific development inhibitors suitable for use in the present invention include mercaptotetrazoles, mercaptotriazoles, dimercaptothiadiazoles, mercaptooxadiazoles, mercaptoimidazoles, mercaptobenzoimidazoles, mercaptobenzoxazoles, mercaptobenzothiazoles, mercaptothiadiazoles, tetrazoles, 1,2,3-triazoles, 1,2,4-triazoles or benzotriazoles.

Representative PUGs suitable for use in the present invention can be found in the following references, all of which are incorporated herein by reference: U.S. Pat. Nos. 3,227,554; 3,384,657; 3,615,506; 3,617,291; 3,733,201 and U.K. Pat. No. 1,450,479 (development inhibitors); U.S. Pat. Nos. 3,880,658; 3,931,144; 3,932,380; 3,932,381; 3,942,987, and 4,840,884 (dye and dye precursors); "On the Chemistry of White Couplers," by W. Puschel, Agfa-Gevaert AG Mitteilungen and der Forschungs-Laboratorium der Agfa-Gevaert AG, Springer Verlag, 1954, pp. 352–367; U.S. Pat. Nos. 2,998,314; 2,808,329; 2,689,793; 2,742,832; German Pat. No. 1,168,769 and U.K. Pat. No. 907,274 (couplers); U.S. Pat. Nos. 2,193,015; 2,108,243; 2,592,364; 3,656,950; 3,658,525; 2,751,297; 2,289,367; 2,772,282; 2,743,279; 2,753,256 and 2,304,953 (developing agents); U.S. Pat. Nos. 3,705,801; 3,715,208; and German OLS No. 2,405,279 (bleach inhibitors); U.S. Pat. Nos. 4,912,024; 5,063,145, columns 21–22, lines 1–70 and EP Patent No 0,193,389 (bleach accelerators); and U.S. Pat. Nos. 4,209,580; 4,463,081; 4,471,045; and 4,481,287 and in published Japanese Patent Application No. 62-123,172 (electron transfer agents).

Specific couplers suitable for use in the present invention are as follows:

DIR coupler I-1

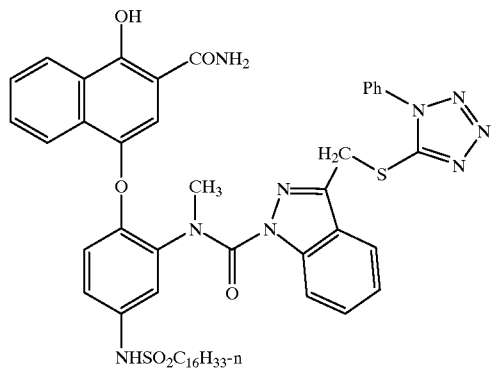

DIR coupler I-2
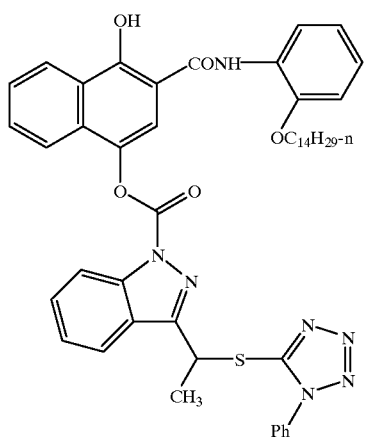
DIR coupler I-3
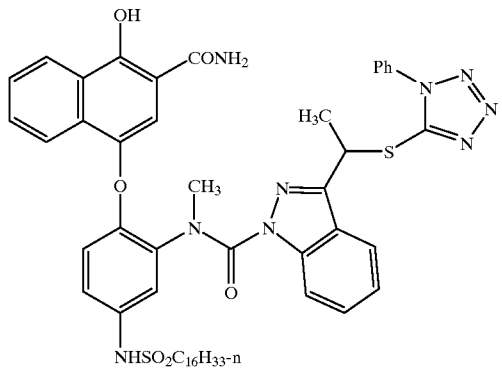
DIR coupler I-4
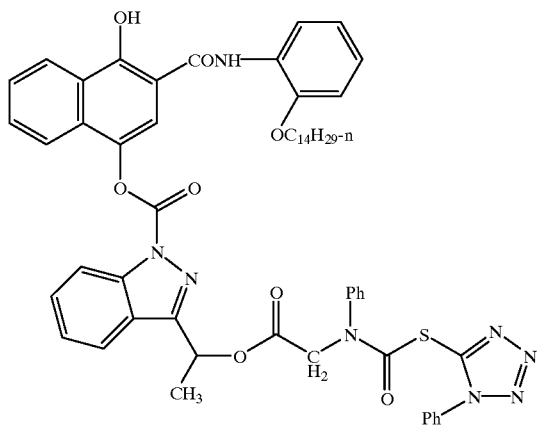
DIR coupler I-5
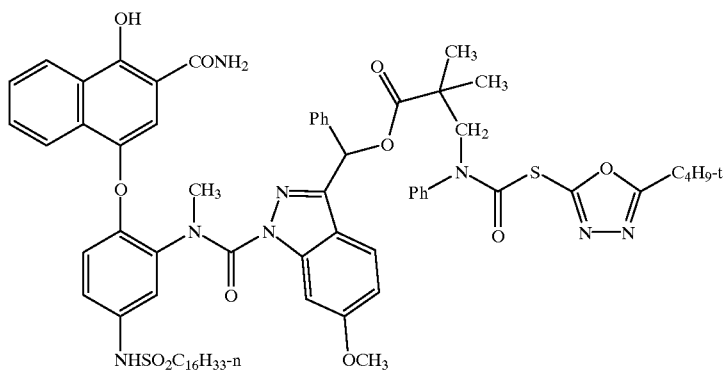

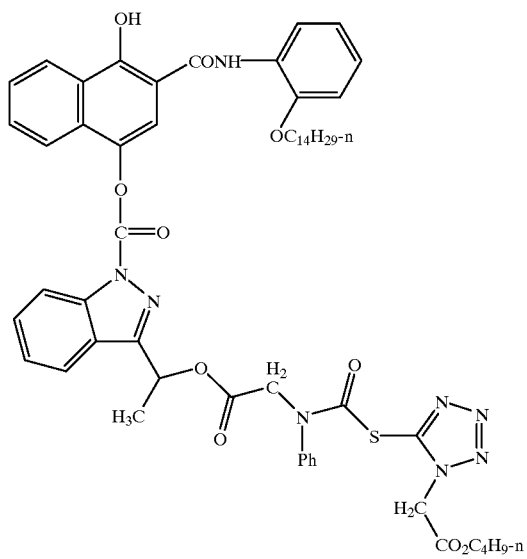
DIR coupler I-6
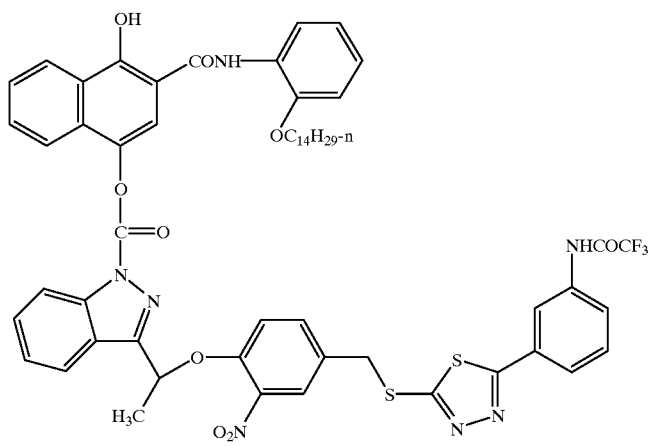
DIR coupler I-7
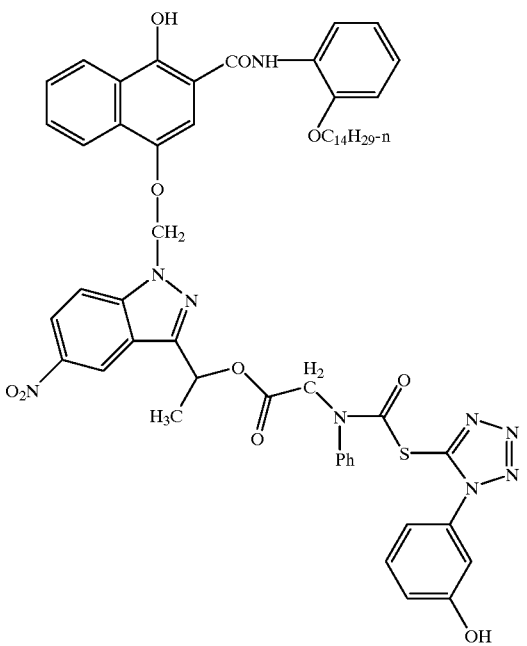
DIR coupler I-8

-continued
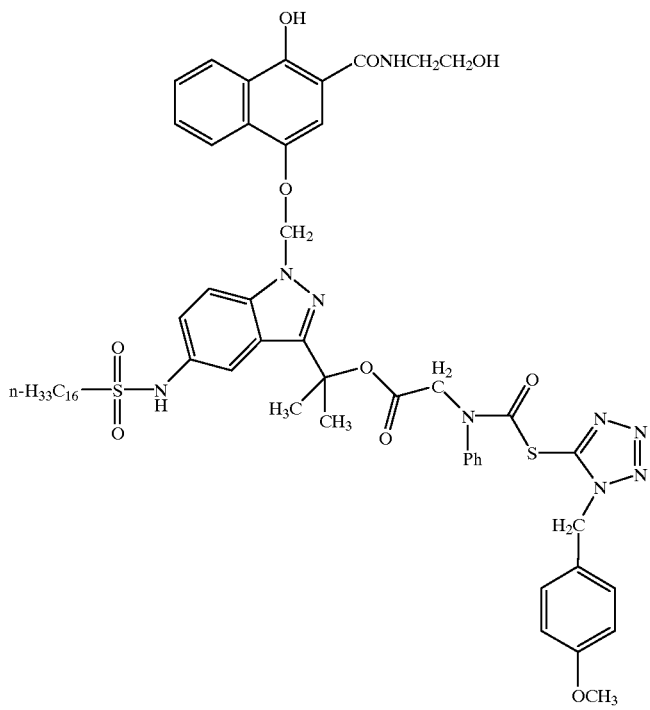
DIR coupler I-9
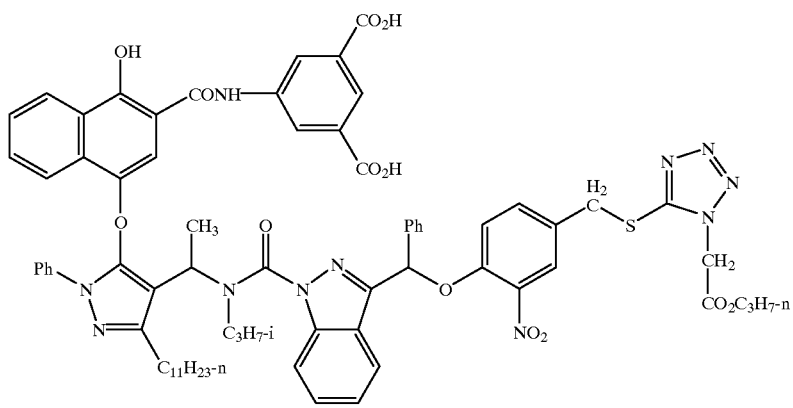
DIR coupler I-10
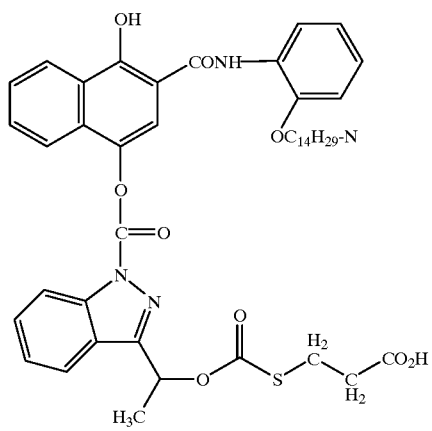
BAR coupler I-11

-continued
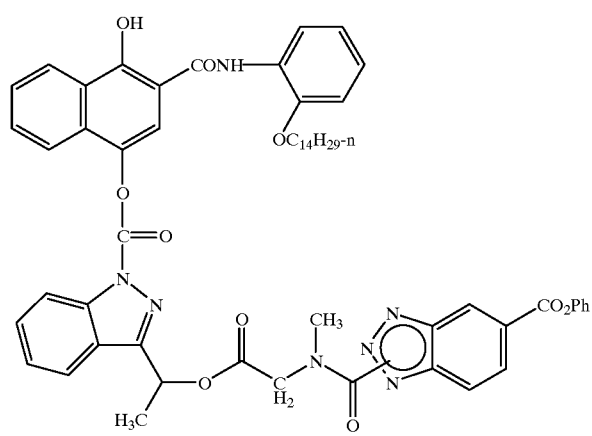
DIR coupler I-12
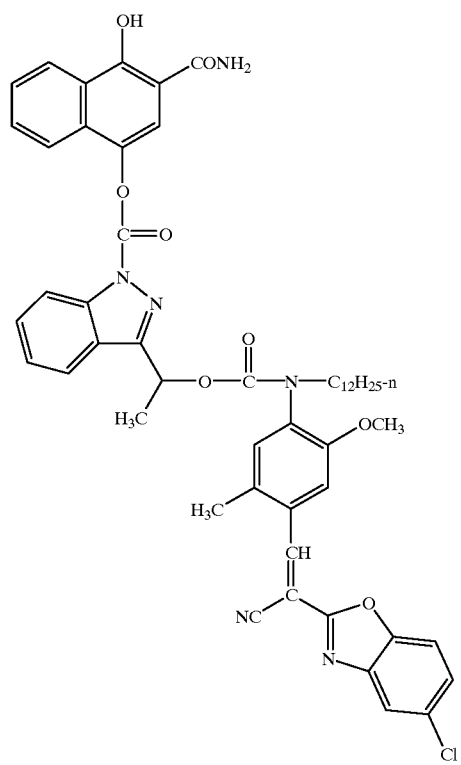
Coupler I-13

Coupler I-14
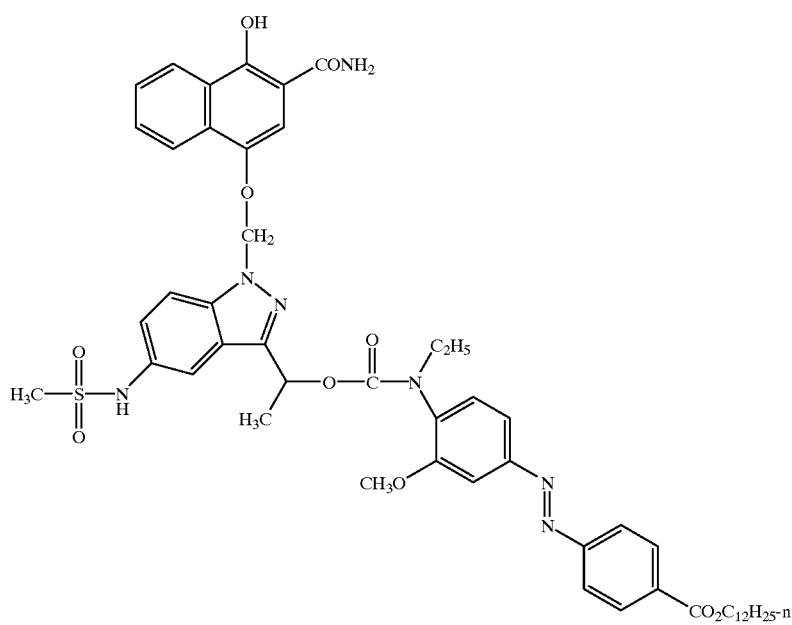
Coupler I-15
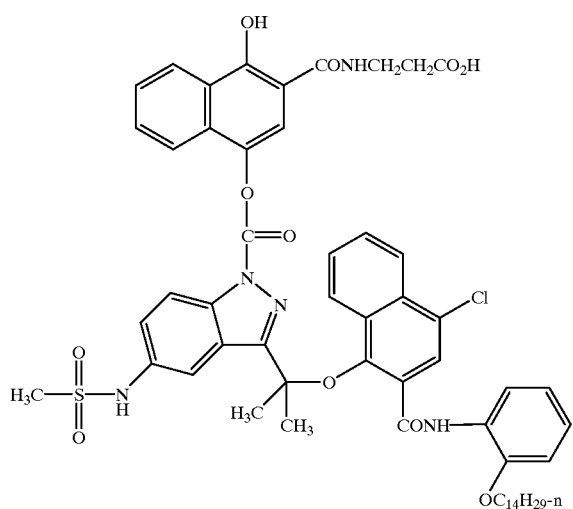
DIR coupler I-16
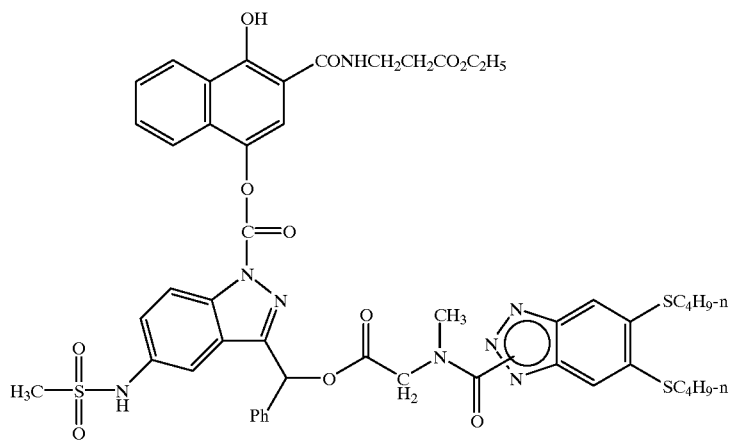

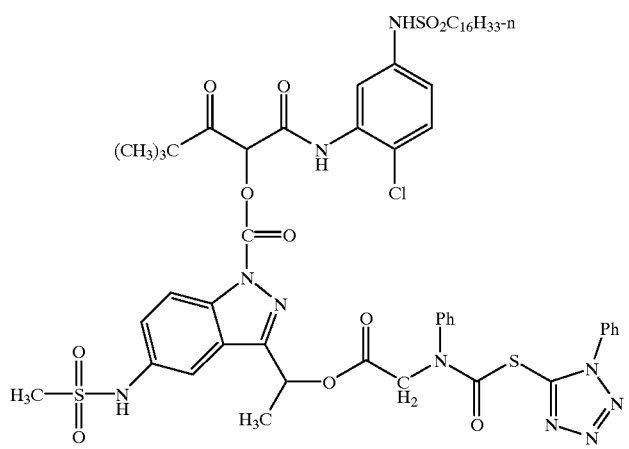
DIR coupler I-17
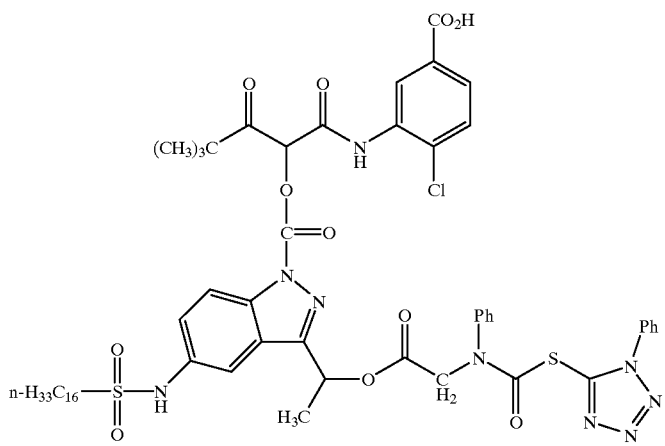
DIR coupler I-18
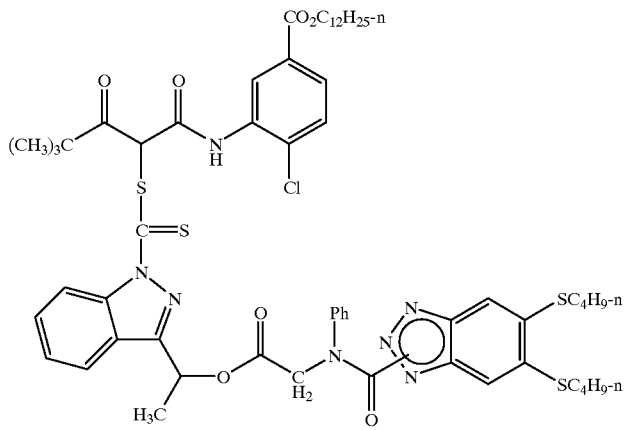
DIR coupler I-19

DIR coupler I-20

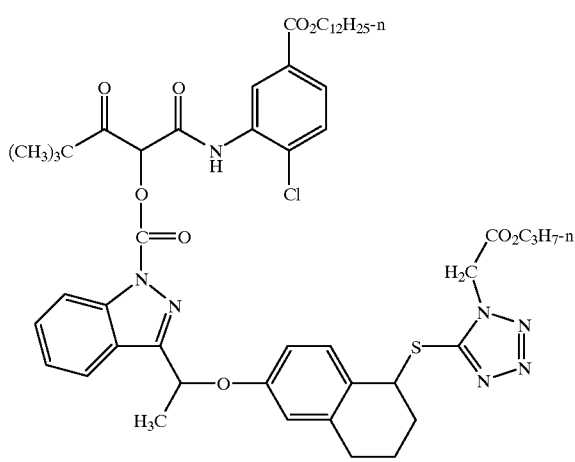

DIR coupler I-21

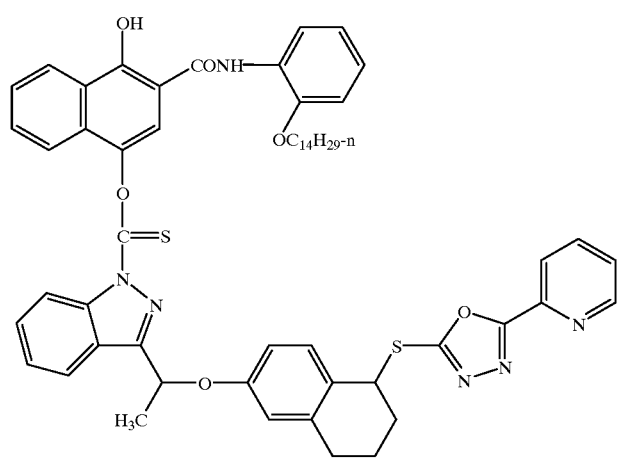

DIR coupler I-22

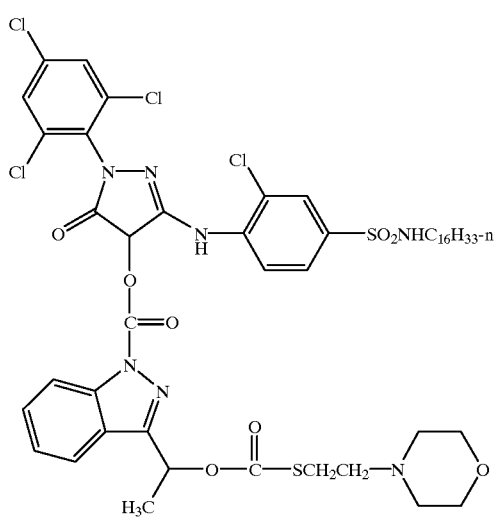

The photographic couplers can be incorporated into photographic elements by means and processes known in the photographic art. Photographic elements in which the couplers are incorporated can be simple elements comprising a support and a single silver halide emulsion layer or multilayer, multicolor elements. The couplers can be incorporated in at least one of the silver halide emulsion layers and/or in at least one other layer, such as an adjacent layer, where they will come into reactive association with oxidized color developing agent which has developed silver halide in the emulsion layer.

The silver halide emulsion layer can contain or have associated with it other photographic couplers such as dye-forming couplers, colored masking couplers, and/or competing couplers. These other photographic couplers can form dyes of any color and hue. Additionally, the silver halide emulsion layers and other layers of the photographic element can contain addenda conventionally contained in such layers.

A typical multilayer, multicolor photographic element can comprise a support having thereon a red-sensitive silver halide emulsion unit having associated therewith a cyan dye imageproviding material, a green-sensitive silver halide emulsion unit having associated therewith a magenta dye image-providing material and a blue-sensitive silver halide emulsion unit having associated therewith a yellow dye image-providing material, at least one of the silver halide emulsion units or another layer having associated therewith a photographic coupler as described above. Each silver halide emulsion unit can be composed of one or more layers and the various units and layers can be arranged in different locations with respect to one another.

The light sensitive silver halide emulsions can include coarse, regular or fine grain silver halide crystals or mixtures thereof, in a hydrophobic colloid, such as gelatin. The crystals can be comprised of silver chloride, silver bromide, silver bromoiodide, silver chlorobromide, silver chloroiodide, silver chlorobromoiodide and mixtures thereof. The emulsions can be negative-working or positive-working emulsions and can be incorporated into negative or reversal elements, as well as other types of elements known in the art. They can form latent images predominantly on the surface of the silver halide grains or predominantly on the interior of the silver halide grains. They can be chemically and spectrally sensitized by methods known in the art.

The photographic element may contain a transparent magnetic recording layer such as a layer containing magnetic particles on the underside of a transparent support, as in U.S. Pat. Nos. 4,279,945 and 4,302,523 and *Research Disclosure,* November 1993, Item 3490, which are incorporated herein by reference. Typically, the element will have a total thickness (excluding the support) of from about 5 to about 30 microns.

The photographic elements can be incorporated into exposure structures intended for repeated use or exposure structures intended for limited use, variously referred to as single use cameras, lens with film, or photosensitive material package units.

The photographic elements can be exposed with various forms of energy which encompass the ultraviolet, visible, and infrared regions of the electromagnetic spectrum as well as with electron beam, beta radiation, gamma radiation, x-ray, alpha particle, neutron radiation, and other forms of corpuscular and wave-like radiant energy in either noncoherent (random phase) forms or coherent (in phase) forms, as produced by lasers. When the photographic elements are intended to be exposed by x-rays, they can include features found in conventional radiographic elements.

The photographic elements are preferably exposed to actinic radiation, typically in the visible region of the spectrum, to form a latent image, and then processed to form a visible dye image. Development is typically followed by the conventional steps of bleaching, fixing, or bleach-fixing, to remove silver or silver halide, washing, and drying.

In the following Table, reference will be made to (1)*Research Disclosure,* December 1978, Item 17643, (2)*Research Disclosure,* December 1989, Item 308119, (3)*Research Disclosure,* September 1994, Item 36544, all published by Kenneth Mason Publications, Ltd., Dudley Annex, 12a North Street, Emsworth, Hampshire PO10 7DQ, ENGLAND, the disclosures of which are incorporated herein by reference. The Table and the references cited in the Table are to be read as describing particular components suitable for use in the photographic element according to the invention. The Table and its cited references also describe suitable ways of exposing, processing and manipulating the elements, and the images contained therein.

| Reference | Section | Subject Matter |
| --- | --- | --- |
| 1 | I, II | Grain composition, morphology |
| 2 | I, II, IX, X, XI, XII, XIV, XV | and preparation; Emulsion preparation including hardeners, |
| 3 | I, II, III, IX A & B | coating aids, addenda, etc. |
| 1 | III, IV | Chemical sensitization and |
| 2 | III, IV | spectral sensitization/ |
| 3 | IV, V | desensitization |
| 1 | V | UV dyes, optical brighteners, |
| 2 | V | luminescent dyes |
| 3 | VI | |
| 1 | VI | Antifoggants and stabilizers |
| 2 | VI | |
| 3 | VII | |
| 1 | VIII | Absorbing and scattering |
| 2 | VIII, XIII, XVI | materials; Antistatic layers; matting agents |
| 3 | VIII, IX C & D | |
| 1 | VII | Image-couplers and image- |
| 2 | VII | modifying couplers; Dye |
| 3 | X | stabilizers and hue modifiers |
| 1 | XVII | Supports |
| 2 | XVII | |
| 3 | XV | |
| 3 | XI | Specific layer arrangements |
| 3 | XII, XIII | Negative working emulsions; Direct positive emulsions |
| 2 | XVIII | Exposure |
| 3 | XVI | |
| 1 | XIX, XX | Chemical processing; |
| 2 | XIX, XX, XXII | Developing agents |
| 3 | XVIII, XIX, XX | |
| 3 | XIV | Scanning and digital processing procedures |

Synthetic Example

The following synthetic example illustrates the synthesis of a coupler suitable for use in the invention. It is intended to be illustrative, and can be readily modified by one of ordinary skill in the art to obtain other suitable couplers.

Synthesis of DIR Coupler I-4

Intermediate A-1

Indazole-3-carboxaldehyde (6.9 g, 47.2 mMole) was suspended in dry diethyl ether (100 mL), under nitrogen, and dry tetrahydrofuran was added until dissolution was achieved. This solution was cooled to 0° C. To the cold solution, a 3M-solution of methylmagnesium bromide (34.5 mL) was added, under nitrogen, keeping the temperature of the solution below 10° C. After the addition of the methylmagnesium bromide, the solution was stirred for 1 hour until it reached room temperature. The solution was then diluted with ethyl acetate and washed with a saturated sodium chloride solution. The organic layer was then collected, dried over magnesium sulfate, filtered and concentrated under reduced pressure to yield Intermediate A-1.

Intermediate A-2

Intermediate A-1 (10.0 g, 61.6 mMole) was dissolved in dry tetrahydrofuran (100 mL), to which was added dry pyridine (5.0 mL, 61.6 mMole). The solution was cooled with ice water and p-nitrophenyl chloroformate (12.43 g, 61.6 mMole) was added. The reaction mixture was stirred at room temperature for 15 minutes, then diluted with ethyl acetate. The ethyl acetate layer was washed with 2N—HCl (2×50 mL). The organic layer was then collected, dried over magnesium sulfate, filtered and concentrated under reduced pressure to yield Intermediate A-2.

Intermediate A-3

Intermediate A-2 (5.0 g, 15.3 mMole), chloroacetic anhydride (2.74 g, 16.0 mMole), and dry pyridine (1.3 mL, 16.0 mMole) were dissolved in tetrahydrofuran (50 mL). This solution was heated to 55° C. for 8 hours, cooled and concentrated. The oil obtained, Intermediate A-3, was used in the next step.

Intermediate A-5

Intermediate A-3 (15.3 mMole) and 1,4-dihydroxy-N-(2-tetradecyloxy)phenyl-naphthalene-2-carboxamide, A-4, (7.15 g, 14.5 mMole), were dissolved in dichloromethane (100 mL). To this solution was added N,N-diisopropyl ethylamine (6.6 mL, 38.2 mMole). The solution was stirred under nitrogen for 3 hours and then diluted with dichloromethane. The dichloromethane solution was washed with 2N—HCl (2×50 mL). The organic layer was collected, dried over magnesium sulfate, filtered and concentrated under reduced pressure to yield crude product. This crude material was dissolved in a mixture of ethyl acetate:dichloromethane:heptane (10:10:85), and subjected to medium pressure column chromatography over silica gel eluting with ethyl acetate:dichloromethane:heptane (10:5:85). The first major band was collected and the solution was concentrated to yield Intermediate A-5 as a tan-white solid.

Intermediate A-6

Intermediate A-5 (3.0 g, 4.0 mMole) was dissolved in dry dimethylforamide (30 mL). To this solution was added potassium iodide (0.99 g, 5.9 mMole) followed by aniline (1.84 mL, 19.8 mMole). The resulting solution was stirred at room temperature for 3 hours and then at 50° C. for 30 minutes. After heating, the solution was cooled, diluted with ethyl acetate washed with 2N—HCl (2×50 mL). The organic layer was then collected, dried over magnesium sulfate, filtered and concentrated under reduced pressure to yield Intermediate A-6.

Intermediate A-7

Intermediate A-6 (4.0 mMole) was dissolved in dry tetrahydrofuran (50 mL). To this solution was added a 20% solution of phosgene in toluene (3.9 mL, 7.9 mMole). The resulting solution was stirred at room temperature for 15 minutes. The solution was then concentrated under reduced pressure to yield Intermediate A-7.

DIR Coupler I-4

Intermediate A-7 (4.0 mMole), was dissolved in dry pyridine (30 mL), to which was added the sodium salt of phenyl mercaptotetrazole (0.87 g, 4.35 mMole). The resulting solution was stirred under nitrogen at room temperature for 45 minutes. At the end of this period the solution was diluted with ethyl acetate, and washed with 2N—HCl (2×50 mL). The organic layer was then collected, dried over magnesium sulfate, filtered and concentrated under reduced pressure to yield the crude product. This crude material was dissolved in a mixture of ethyl acetate:dichloromethane:heptane (20:10:80), and subjected to medium pressure column chromatography over silica gel eluting with the same solvent mixture. The first major band was collected and the solution was concentrated to yield DIR Coupler I-4.

The above synthesis can be represented by the following scheme:

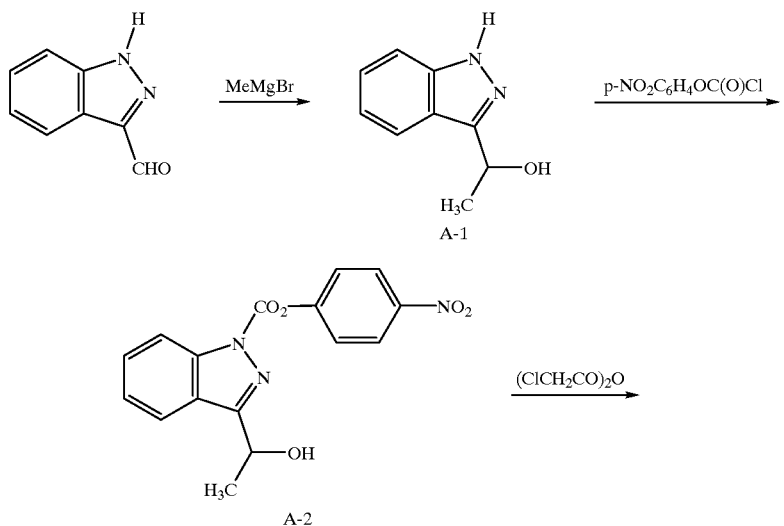

-continued
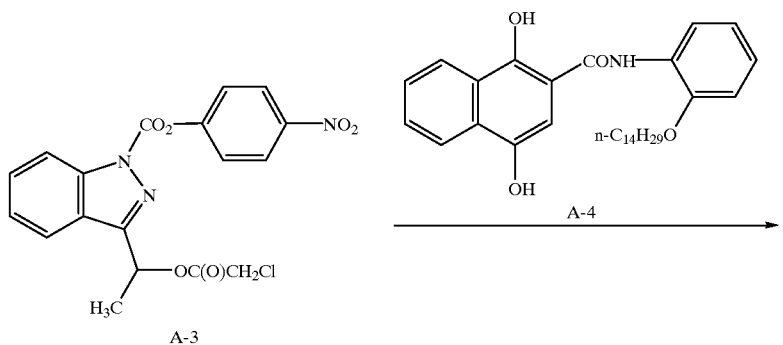
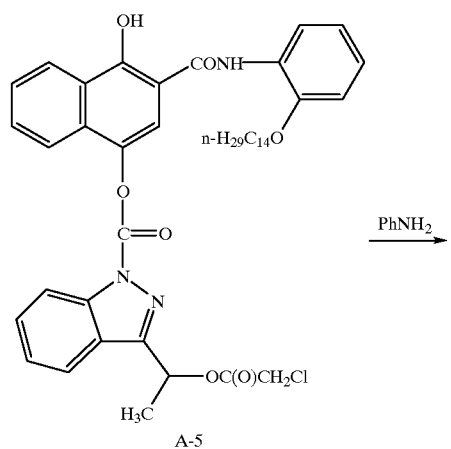
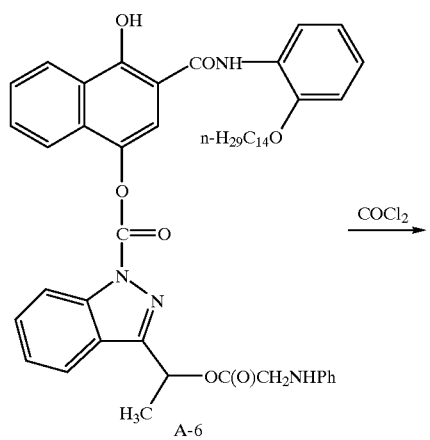
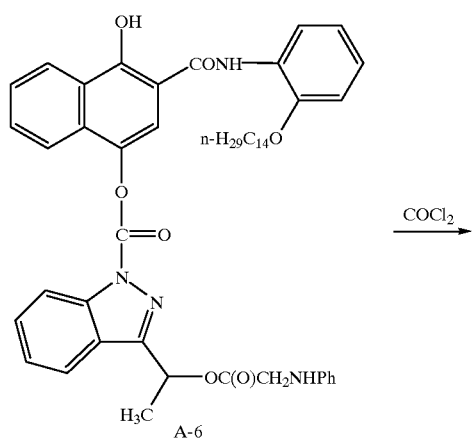

-continued

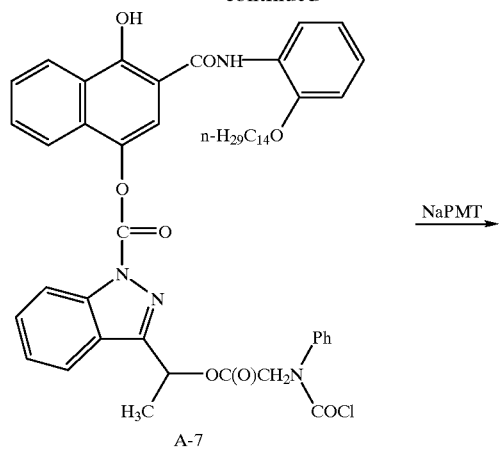
A-7

NaPMT →

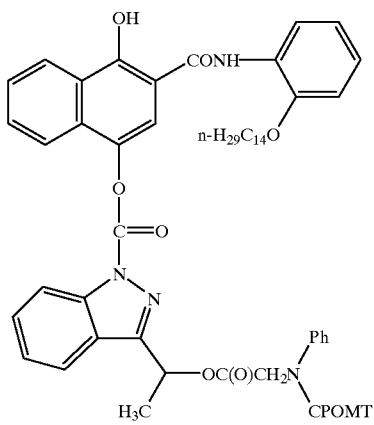
DIR Coupler I-4

The following example illustrates the practice of the invention. It is intended to be illustrative, and should not be construed as limiting the invention to the specific embodiments disclosed.

EXAMPLE

Photographic elements were prepared by coating the following layers on a cellulose ester film support (amounts of each component are indicated in mg/m$^2$):

| Emulsion layer 1: | Gelatin-2420; red sensitized silverbromoiodide (as Ag)-1615; yellow image coupler (Y-1)-1291, dispersed in dibutyl phthalate. |
|---|---|
| Interlayer | Gelatin-860; didodecylhydroquinone-113 |
| Emulsion layer 2: | Gelatin-2690; green sensitized silver bromoiodide (as Ag)-1615; magenta image coupler (M-1)-898, dispersed in tritolyl phosphate; DIR coupler of Tables 1 and 2 dispersed in N,N-diethyl-dodecanamide. |
| Protective Overcoat | Gelatin-5380; bisvinylsulfonylmethyl ether at 2% total gelatin. |

Structures of compounds utilized in the Examples and not previously described are as follows:

Magenta Image Cuopler, M-1:

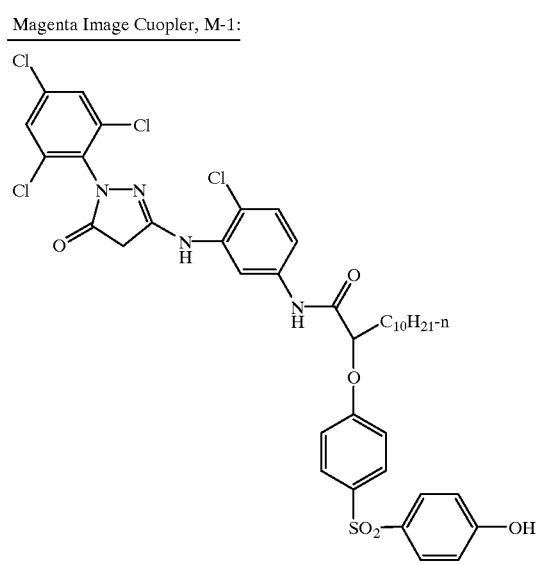

Yellow Image Coupler, Y-1:

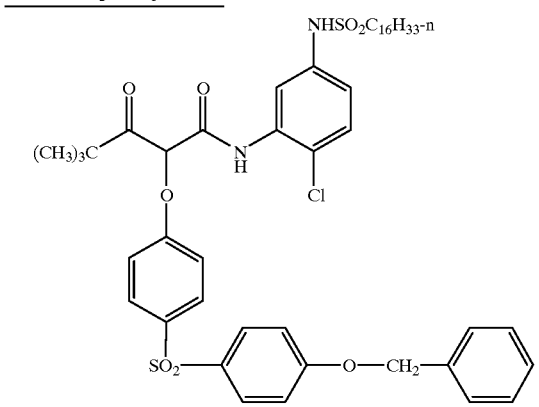

DIR Coupler: C-1

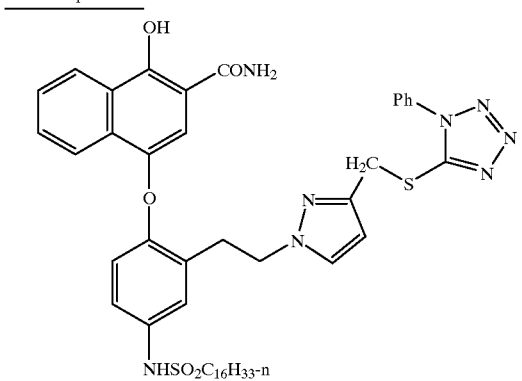

Strips of each element were exposed to green light through a graduated density step tablet or through a 35% modulation fringe chart for sharpness measurements, and then developed for 3.25 minutes at 38° C. in the following color developer. Development was then stopped, and the elements washed, bleached, fixed, washed and dried.

| Color Developer | |
|---|---|
| Distilled water | 800 mL |
| Sodium Metabisulfite | 2.78 g |
| Sodium Sulfite, anhydrous | 0.38 g |
| CD-4 (color developer)* | 4.52 g |
| Potassium Carbonate, anhyd. | 34.3 g |
| Potassium Bicarbonate | 2.32 g |
| Sodium Bromide | 1.31 g |
| Potassium Iodide | 1.20 mg |
| Hydroxylamine Sulfate | 2.41 g |
| Diethylenetriaminepentacetic acid, pentasodium salt (40% Soln.) | 8.43 g |
| Distilled water | to 1 L |
| Adjust pH to 10.0. | |

*CD-4 ™ (Eastman Kodak Company) is a color developing solution in which the active component is 4-amino-3-methyl-N-ethyl-N-beta-hydroxyethylaniline sulfate.

Photographic effects were determined as follows: To determine acutance(AMT), a series of elements as described above containing no DIR coupler or varying levels of DIR coupler were exposed with green light. The contrast ($\gamma$) along the straight line portion of each elements' D log H curve was measured. A plot of log($\gamma$) versus amount of DIR coupler ($\mu$moles) was made for each element (each element containing a different DIR coupler). From these plots, the amount of DIR coupler needed to achieve log($0.8\gamma_o$) was read, where $\gamma_o$ represented the contrast of the element containing no DIR coupler. This value was recorded in the Table 1 as Amount (amount of DIR coupler need to reduce the contrast by 20%). In the same experiment, a plot of acutance versus log($\gamma$) was made for each element and from this plot the acutance at position log($0.8\gamma_o$) was read. These acutance values are shown in Table 1.

Acutance, as measured by AMT values and recorded in Table 1, was calculated using the following formula in which the cascaded area under the system modulation curve is shown in equation (21.104) on page 629 of the "Theory of the Photographic Process", 4th Edition, 1977, edited by T. H. James: AMT=100+66Log[cascaded area/2.6696M] wherein the magnification factor M is 3.8 for the 35 mm system AMT. The use of CMT acutance is described by R. G. Gendron in "An Improved Objective Method of Rating Picture Sharpness: CMT acutance" in the Journal of SMPTE, Vol. 82, pages 1009–12, (1973). AMT is a further modification of CMT useful for evaluating systems which include the viewing of a positive print made from a negative.

TABLE 1

| Coupler | Amount ($\mu$Moles/m$^2$) | AMT (35 mm) |
|---|---|---|
| C-1 | 376.6 | 90.6 |
| I-1 | 166.8 | 90.6 |
| I-2 | 21.5 | 91.0 |
| I-3 | 32.3 | 90.7 |
| I-4 | 204.4 | 91.8 |

As the data in Table 1 demonstrates, the couplers utilized in the present invention are more active than comparative compounds. They can thus be coated in photographic emulsions at low levels, thus minimizing the potential that they will react with other components in the emulsion and adversely affect photographic performance. The photographic couplers utilized in the invention, when releasing a development inhibitor, also provide for improved sharpness and contrast reduction.

Table 2, below, based on the Example provided above, shows the percentage change in contrast ($\gamma$) for a given amount of each inventive or comparative coupler. As can be seen, the activity of the couplers utilized in the invention is far superior to that of the comparative coupler.

TABLE 2

| Coupler | % $\gamma$ Reduction at 53.8 $\mu$Moles/m$^2$ | % $\gamma$ Reduction at 107.6 $\mu$Moles/m$^2$ | % $\gamma$ Reduction at 161.4 $\mu$Moles/m$^2$ |
|---|---|---|---|
| C-1 | 3.4 | 6.6 | 9.3 |
| I-1 | 6.6 | 13.3 | 19.7 |
| I-2 | 45.2 | 70.5 | 84.2 |
| I-3 | 29.3 | 49.4 | 63.3 |
| I-4 | 4.5 | 11.0 | 16.8 |

The invention has been described in detail with particular reference to preferred embodiments thereof, but it will be understood that variations and modifications can be effected within the spirit and scope of the invention.

What is claimed is:

1. A photographic coupler represented by the formulae:

COUP—T$^1$—T$^2$—(T$^3$)$_b$—PUG wherein

COUP is a coupler moiety having a coupling site to which T¹ is attached;

T¹ is a timing or linking group which releases from COUP during processing and which functions by electron transfer down a conjugated or unconjugated chain, or by nucleophilic displacement reaction, to release T², T² being an indazole timing or linking group which, after release from T¹, functions by electron transfer down a conjugated chain to release T³ or PUG, and which is represented by the formula:

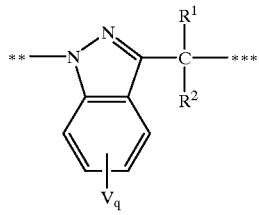

wherein  denotes the point of attachment to T¹ and * denotes the point of attachment to T³ or PUG;

R¹ and R² are independently selected from hydrogen, an aliphatic, carbocyclic, and heterocyclic group, or may be bonded together to form a 5, 6, or 7 membered ring;

V is independently selected from the group consisting of an alkyl, carbocyclic, heterocyclic, halo, carbamoyl, sulfamoyl, carbonamido, sulfonamido, keto, sulfo, nitro, hydroxyl, carboxyl, amino, alkoxy, alkoxycarbonyl, aryloxy, and arylthio group;

q is 0, 1, 2, 3 or 4;

T³ is a timing or linking group attached to T² which is released therefrom after T² releases from T¹, and which functions by electron transfer down a conjugated or unconjugated chain, or by nucleophilic displacement reaction, to release PUG;

b is 0 or 1; and

PUG is a photographically useful group.

2. A photographic coupler represented by the formula:

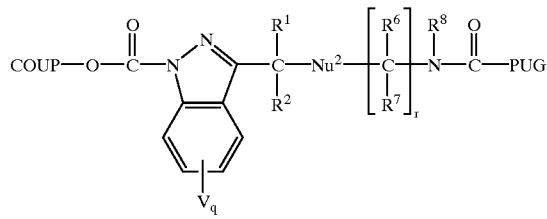

wherein

COUP is a coupler moiety;

R¹ and R² are independently selected from hydrogen, an aliphatic, carbocyclic, and heterocyclic group, or may be bonded together to form a 5, 6, or 7 membered ring;

V is independently selected from the group consisting of an alkyl, carbocyclic, heterocyclic, halo, carbamoyl, sulfamoyl, carbonamido, sulfonamido, keto, sulfo, nitro, hydroxyl, carboxyl, amino, alkoxy, alkoxycarbonyl, aryloxy, and arylthio group;

q is 0, 1, 2, 3 or 4;

Nu² is a nucleophilic group;

R⁶, R⁷ and R⁸ are independently selected from hydrogen, an aliphatic, carbocyclic, and heterocyclic group, or two of R⁶, R⁷ and R⁸ may be bonded together in a pair to form a 5, 6, or 7 membered ring; and r is selected from 0, 1, 2, 3, 4 or 5 and;

PUG is a photographically useful group.

* * * * *